(12) United States Patent
Andrus et al.

(10) Patent No.: US 6,450,971 B1
(45) Date of Patent: Sep. 17, 2002

(54) TEMPERATURE MEASURING BALLOON

(75) Inventors: W. Scott Andrus, Eden Prairie; Jaydeep Y. Kokate, Maple Grove; Bruce Persson, New Brighton; Eric DoBrava, Crystal, all of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/679,966

(22) Filed: Oct. 5, 2000

(51) Int. Cl.⁷ .................................................. A61B 5/00
(52) U.S. Cl. ........................................................ 600/549
(58) Field of Search ................................. 600/549, 587; 607/101, 99, 88–114

(56) References Cited

U.S. PATENT DOCUMENTS

| | | |
|---|---|---|
| 3,533,399 A | 10/1970 | Goldberg et al. |
| 3,661,148 A | 5/1972 | Kolin |
| 3,847,139 A | 11/1974 | Flam |
| 4,046,139 A | 9/1977 | Horn |
| 5,010,892 A | 4/1991 | Colvin et al. |
| 5,316,016 A | 5/1994 | Adams et al. |
| 5,752,522 A | 5/1998 | Murphy |
| 5,935,075 A | 8/1999 | Casscells et al. |

OTHER PUBLICATIONS

U.S. application No. 08/951769, Ren et al., filed Oct. 16, 1997.

*Primary Examiner*—Kevin Shaver
*Assistant Examiner*—Pamela Wingood
(74) *Attorney, Agent, or Firm*—Vidas, Arrett & Steinkraus, P.A.

(57) ABSTRACT

A balloon catheter for locating vulnerable plaque lesions within a body lumen comprising a unique balloon mounted on a catheter shaft. The balloon having an uninflated state and being expandable to an inflated state, the balloon further having an inside and an outside, the balloon being made at least partially of at least one temperature responsive material. The at least one temperature responsive material designed to exhibit at least one predetermined color when the material is in contact with an object having an elevated temperature, such as a vulnerable plaque lesion. The catheter having a lumen which allows a light source to transmit light into the inside of the balloon. The light directed to illuminate at least a portion of the temperature responsive material. A light detector positioned to detect the light reflected off of the portion of the temperature responsive material to provide indicate the presence of the suspected lesion based on one or more characteristic changes to the light reflected from the temperature responsive material.

35 Claims, 3 Drawing Sheets

TEMPERATURE MEASURING BALLOON

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates to the detection of lesions within a body vessel. More specifically, the present invention is directed to the detection of vulnerable plaque legions by inserting a balloon into a body vessel, wherein the balloon is at least partially composed of material having temperature dependent properties which are optically detectable from within the balloon during use. The present invention utilizes a temperature responsive balloon material which exhibits a detectable change in at least one optical property such as color, reflectivity, optical density, polarization, etc. when in immediate proximity to the higher temperature of a vulnerable plaque lesion.

2. Description of the Related Art

It is widely recognized that plaques or lesions may be classified into three broad categories: calcified or hard plaque lesions, fibrous or soft lesions and inflamed soft lipid filled plaques or lesions. The diagnosis of the type of lesion drives the particular treatment of the lesion, whether it is removal of the lesion by rotablator, predilatation by balloon angioplasty, delivery of a stent, with or without predilatation, or the like.

In particular, the identification of inflamed plaques or lesions is important since these lesions are at greatest risk of rupture, which can lead to a large thrombus or blood clot, which can completely occlude the flow of blood through the artery, leading to injury of the heart or brain. An inflamed or vulnerable lesion is characterized by its cap thickness, lipid pool size and inflammation or temperature. This is discussed in great detail in U.S. Pat. No. 5,935,075, the entire contents of which are hereby incorporated by reference. As discussed in U.S. Pat. No. 5,935,075, considerable evidence indicates that plaque rupture triggers 60–70% of fatal myocardial infarctions. An inflamed plaque is hotter than the surrounding tissue. U.S. Pat. No. 5,935,075 relates to using an infrared fiber optic system to locate inflamed heat producing plaque by detecting the infra-red radiation absorbed by the balloon to a detector and signal fiber. However, the device described therein is very expensive, making it available in a limited number of procedures. What is needed is a more inexpensive method for classifying plaques or lesions, and in particular determining which plaques are hard, soft or inflamed, which drives the treatment after diagnosis.

In copending application Ser. No. 08/951,769, entitled Thermal and Stress Mapping of Body Lumens, commonly assigned and incorporated herein by reference in its entirety, there is described a technique for measuring lesion temperature by analyzing stress patterns in a lesion molding balloon which are revealed under a polariscope after the balloon has been molded to the lesion and then removed from the body for inspection. In this same application it has alternatively been suggested to use a balloon coating which changes color in accordance with a temperature experience.

Many materials are known which, within a defined temperature range change color in accordance with the then current temperature. Many such materials, however, are reversible, so that the observed color (within a material response time lag) is reflective of the real time temperature, not a past temperature history. Such materials would not be suitable to use in the system of application Ser. No. 08/951,769, since the lesion temperature is not read until the balloon has removed from the body.

As a result, it is clear that there is a continued need for a relatively inexpensive means of detecting vulnerable plaque within the body using a balloon having a temperature responsive material which produces a detectable change which may be detected and/or observed while the balloon remains in the body.

BRIEF SUMMARY OF THE INVENTION

This invention provides for a balloon catheter which may be inserted into a body lumen and advanced to the suspected location of a vulnerable plaque lesion. At least a portion of the balloon material is comprised of a temperature responsive material such as a thermochromic cholesteric liquid crystal material or materials which produces an optically detectable property change when the material is exposed to increases in temperature. For instance thermometers using cholesteric liquid crystal such as those available from Hallcrest, Inc. are known to display a specific color when a given temperature is reached or exceeded. Materials exhibiting a color change or other type of detectable change in an optical property, such as: a change in polarization, optical density, reflectivity, etc.; when the material is subjected to a predetermined temperature may be suitable for use in the present invention.

Because the balloon includes material having such temperature indicating property, or properties, when the balloon is inflated to be in contact with a vulnerable plaque lesion, the higher temperature of the lesion will be detected by analyzing a beam of light which is directed on to the suspected lesion site and the balloon material in contact therewith. In at least one embodiment of the invention the light may allow a user to directly observe a change in the balloon material such as a color change, alternatively a detector may be used to detect changes such as a change in the materials reflectivity as a result of the increase in temperature.

Because many thermochromic cholesteric liquid crystal materials provide a real-time indication of temperature, it is desirable to observe the property change(s) of the balloon material while it is in contact with the lesion site. In at least one embodiment of the present invention, the balloon material may be directly observed in situ, from within the expanded balloon, by providing the catheter with at least one light source which may be used to transmit light into the balloon to illuminate the balloon interior so that any potential coloring, or other physical change, of the material may be detected by a light detecting device or a viewing device to provide for direct observation by a practitioner. By detecting and/or viewing the color, or other property change in the material or light reflected therefrom, the practitioner is able to confirm the location of a lesion in real time. If no color change or other property change is detected, the balloon may be deflated and advanced to another site, where the balloon may once again be inflated and potential changes observed.

In light of the above, the present invention provides for a catheter that may provide real time location and imaging of vulnerable plaque lesions.

In at least one embodiment of the invention a catheter is provided which has a balloon, the balloon being capable of repeated inflation and deflation so that with a single use the catheter may be used to locate one or more lesions which may be located along the length of a body vessel or lumen.

In at least one embodiment, the balloon catheter of the present invention may be incorporated into other devices and/or incorporate other devices. For example the present invention may be equipped with a second balloon which may be employed to deliver a stent to a lesion site detected by the thermochromatic balloon of the present invention. Such hybrid devices could allow a single catheter to be used for detection and treatment of a lesion, thereby avoiding the need to employ multiple catheters and thus multiple medical procedures.

In addition to the apparatus described above, the present invention as described above is directed also to the inventive method described which requires advancing the balloon catheter to the suspected site of a lesion, inflating the balloon to contact the lesion, after an equilibration time illuminating the balloon surface from within the balloon by transmission of light from a light source positioned alternatively within the balloon or outside of the balloon, directing the light onto the portion of the balloon in contact with the lesion, and then detecting the light reflected from the balloon material with a detector or through direct visual inspection.

Direct detection and/or observation of changes in the balloon material via reflected light may allow a user to produce a temperature map of the lesion. By referencing the shape of the lesion as indicated by the observed deformation of the inflated balloon and the optical properties of the balloon material, a temperature map may be generated which can be used to determine whether a lesion is an inflamed vulnerable lesion which is at greatest risk of rupture. The observed properties of the material at a lesion site may also be used to determine whether the lesion is a hard calcified lesion or other type of lesion.

BRIEF DESCRIPTION OF THE SEVERAL VIEWS OF THE DRAWINGS

A detailed description of the invention is hereafter described with specific reference being made to the drawings in which:

FIG. 5 is a diagrammatic view of the light pathway of the embodiment of the invention shown in FIG. 2; and.

DETAILED DESCRIPTION OF THE INVENTION

Figure 1:
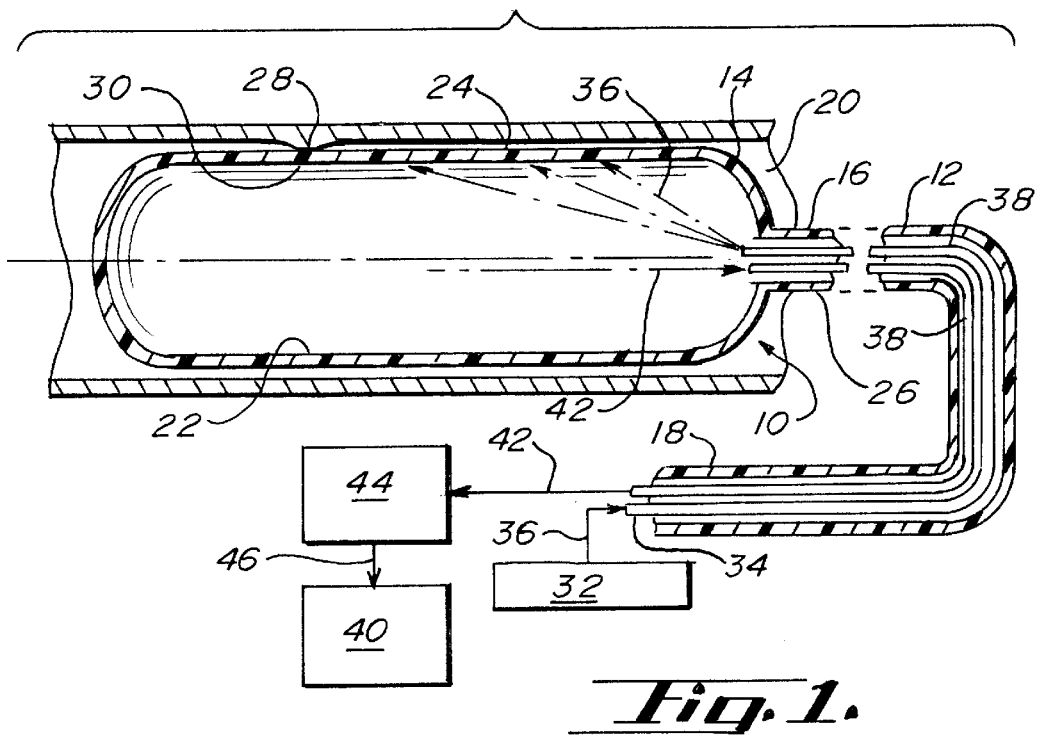
FIG. 1 is a side view of an embodiment of the invention.

In the embodiment of the invention shown in FIG. 1, the balloon catheter, indicated generally by reference numeral 10, may be seen to have a catheter shaft 12 with a medical balloon 14 mounted thereupon. As may be seen the catheter shaft 12 has a distal end 16 and a proximal end 18. In the embodiment shown the balloon 14 is mounted on the distal end 16 of the catheter shaft 12, however, in alternative embodiments the balloon 14 may be mounted at any location along the catheter shaft 12. In the embodiment shown the distal end 16 of the catheter shaft 12 is inserted into a body lumen or vessel 20, where as the proximal end 18 remains outside the body lumen 20.

The balloon 14 has an inside 22 and an outside 24. The balloon 14 is expandable between an unexpanded state and an expanded state. The balloon 14 is in fluid communication with an inflation lumen 26. When the balloon 14 is advanced to a predetermined location within the vessel 20, fluid may be passed from the proximal end 18, through the inflation lumen 26 into the inside 22 of the balloon 14 to provide for expansion of the balloon 14. When the balloon is expanded to the expanded state, the outside 24 of balloon 14 will contact the site of a suspected lesion 28.

As indicated above the material of the balloon includes at least one temperature responsive material which when subjected to elevated temperatures will exhibit a change in color and/or changes in other optically detectable physical characteristics as well. It is known that vulnerable plaque lesions tend to be approximately 2–3 degrees (Celsius) warmer than the surrounding vessel. As a result, when the temperature responsive material 30 of balloon 14 is in contact with a lesion 28, in at least one embodiment of the invention, the relatively higher temperature of the lesion 28 will cause the material 30 to change color. For example the material 30 may exhibit a substantially uniform color, such as gray or black when exposed to the temperature of a body lumen. The material may change from this first color to a second color, such as red or yellow when the material is exposed to a 1 or 2 degree increase in temperature.

In at least one embodiment the material 30 may also be provided with the ability to change to additional colors as the temperature increases. For example, a three degree increase in temperature may result in a third color such as green or blue; a four degree increase in temperature may result in the material transitioning back to its original color or the material may exhibit yet another color.

depending on the specific characteristics of the temperature responsive material, a plurality of colors, or other property changes may be provided for. In the embodiment where color change is indicative of elevated temperatures, a specific color may be attributable to a specific temperature throughout a predetermined temperature range. As a result, such material 30 may provide a color map of an inflamed lesion 28 wherein the warmer center is depicted by one color and other colors depict the decrease in temperature from the warmer center of the lesion to its outer limits.

In the embodiment shown the temperature responsive material 30 is included in the balloon material making up at least the inside 22 of the balloon 14. Alternatively, the temperature responsive material 30 may be a coating applied, selectively or otherwise, to the inside 22 of the balloon 14. The temperature responsive material 30 may also be a fluid which is positioned between the inside 22 and outside 24 of the balloon 14, wherein the inside 22 is transparent.

The temperature responsive material 30 may be a chromatically responsive cholesteric liquid crystal. The material 30 may be comprised of one or more materials selected from the group consisting of: cholesteryl halides; mixed esters of cholesterol and inorganic acids; cholesteryl esters of saturated and unsaturated, substituted and unsubstituted organic acids; cholesteryl ethers and any combinations thereof. The temperature responsive material 30 may include other chromatically responsive substances as are known.

In alternative embodiments of the invention it may be desirable to select specific substances for inclusion into the material 30. In such embodiments the material 30 is selected from one or more of the group consisting of: cholesteryl chloride; combinations of cholesteryl bromide and cholesteryl iodide; cholesteryl nitrate; cholesteryl nonanoate; cholesteryl crotonate; cholesteryl chloroformate; cholesteryl chlorodecanoate; cholesteryl chloroeicosanoate; cholesteryl butyrate; cholesteryl caprate; cholesteryl oleate; cholesteryl linolate; cholesteryl linolenate; cholesteryl laurate; cholesteryl erucate; cholesteryl myristate; cholesteryl clupanodonate; oleyl cholesteryl carbonate; cholesteryl heptyl carbamate, decyl cholesteryl carbonate; cholesteryl p-chlorobenzoate; cholesteryl cinnamate; cholesteryl ethers; cholesteryl decyl ether; cholesteryl lauryl ether; cholesteryl oleyl ether; and any combinations thereof.

In order for the above described color change(s) or other property change(s) to be detected, the present invention may be equipped with a light source which may transmit a predetermined wavelength or wavelengths of light into the inside of the balloon in order to illuminate the material 30. In the embodiment shown in FIG. 1, the light source 32 is positioned at the proximal end 18 of the catheter shaft 12, outside the vessel 20. A fiber optic line 34 transmits the light (indicated by arrow 36) from the light source 32 into the inside 22 of the balloon 14.

As may be seen in FIG. 1, the fiber optic line 34 may be provided with multiple fibers 38 for light transmission and may also include additional fibers for light returning from the interior (returning light) to be detected. Returning light is indicated by arrow 42. The one or more of the additional fibers 38 may be used to provide a direct optical link between the inside 22 of the balloon 14 and the proximal end 18 of the catheter shaft 12, thereby providing a practitioner with the ability to directly observe what the light 36 transmitted into the balloon 14 is illuminating, namely the temperature responsive material 30 and the associated colors thereon.

In at least one embodiment, the fiber(s) 38 may be connected to a detector 40 which may provide an image for the practitioner to inspect. The detector 40 may be a monitor, camera, computer or other device which provides a practitioner with the ability to see the illuminated interior 22 of the balloon 14 and/or detect a the light returning from the material 30. The detector may be designed to detect the entire spectrum of light returning from the material 30 or a predetermined wavelength thereof. The detector may further be constructed to emit a detector signal to indicate a detected change in a property of the light which is indicative of the presence of a lesion. Such properties and their detectable changes may include the aforementioned polarity, optical density, reflectivity, spectrum, wavelength, and/or other light properties.

In at least one embodiment of the invention, the detector may be constructed to provide an indicator signal as to the presence of a predetermined wavelength of light, which would be provided when incoming light 36 is reflected off of the material 30. In such an embodiment it may be necessary to filter undesired spectra of light so that the detector 40 receives the wavelength or spectrum indicative of the elevated temperature of the lesion 28. As a result a filter 44, may be provided which differentially filters out undesired wavelengths of light, and transmits only the wavelength, indicated by arrow 46, associated with the property change (s) of material 30 which may be indicative of the elevated temperature of a lesion 28.

Figure 4:
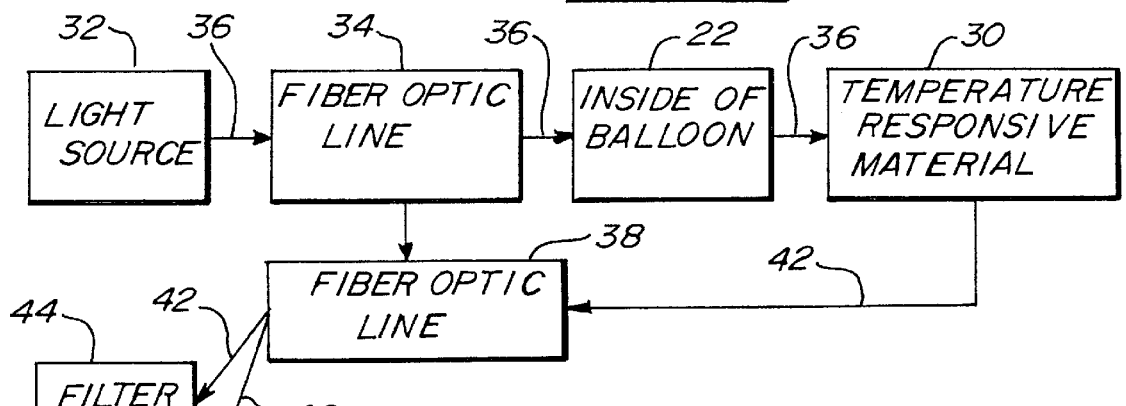
FIG. 4 is a diagrammatic view of the light pathway of the embodiment of the invention shown in FIG. 1.

To better understand the path way of light passing through the potential embodiments described above and shown in FIG. 1, a block diagram is provided in FIG. 4.

As may be seen in FIG. 4, a first predetermined wavelength of light 36 is emitted from light source 32. The light 36 travels along fiber optic line 34 to the inside 22 of the balloon where it illuminates the inside 22 of the balloon including the temperature responsive material 30. Once the light contacts the material 30, the light is at least partially reflected away from the material 30 and may be observed in the form of reflected light 42. Reflected light 42 is passed back through line 34 or a fiber 38 thereof and may be detected by detector 40 where an image or other electronic signal is produced. If desired the reflected light 42 may be passed through a filter 44 which differentially filters the light 42 to allow transmission of only a predetermined wavelength or color of light 46 which is the same as or indicative of the color of the material 30 in contact with a lesion.

Figure 2:
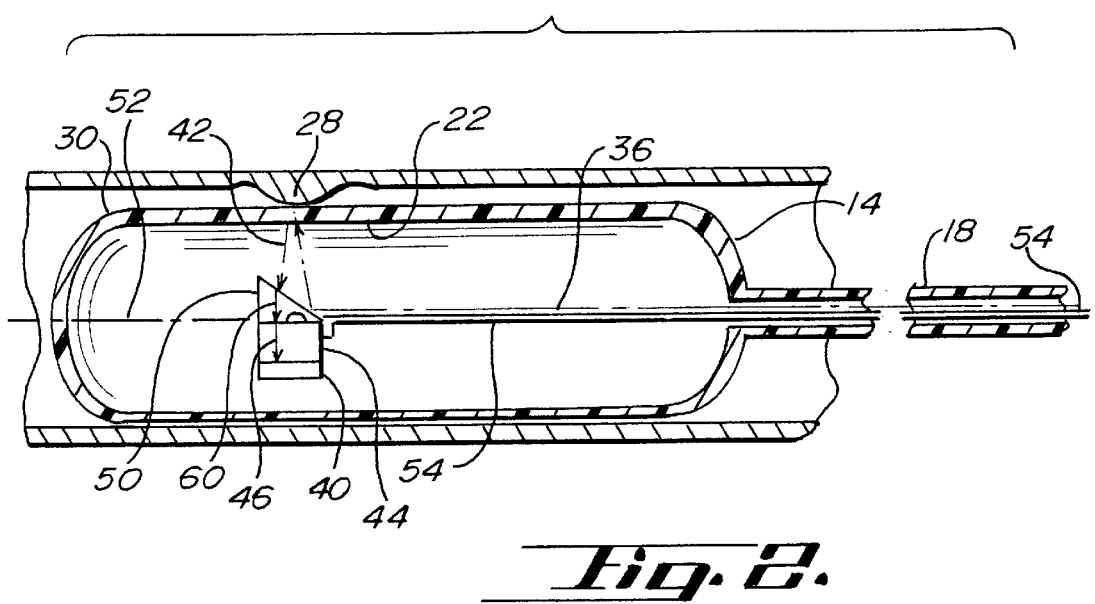
FIG. 2 is a side view of an embodiment of the invention.

Turning to FIG. 2, an alternative embodiment of the invention may be seen wherein a light directing device 50 such as a mirror, reflector, or similar apparatus is positioned within the inside 22 of the balloon 14. The light directing device or director 50 may be fixedly or moveably positioned along the longitudinal axis 52 of the balloon 14. The director may be mounted on a proximally extending member 54 which extends to the proximal end 18. The director 50 directs the light 36 transmitted into the inside 22 of the balloon 14 to a specific location on the inside 22, namely the temperature responsive material 30 in contact with lesion 28.

In order to direct the light 36 about the entire inside 22 of the balloon 14, the director 50 may be moved along the length of the longitudinal axis 52 of the balloon 14 by pushing or pulling the member 54 at the proximal end 18. The director may also be rotated about the longitudinal axis 52 by similarly rotating the member 54 at the proximal end 18. By rotating and moving the director 50 along the longitudinal axis 52 of the balloon 14 the entire inside 22 of the balloon 14 may be inspected for detectable changes in the material 30 which indicate the presence of a lesion 28.

Figure 5:
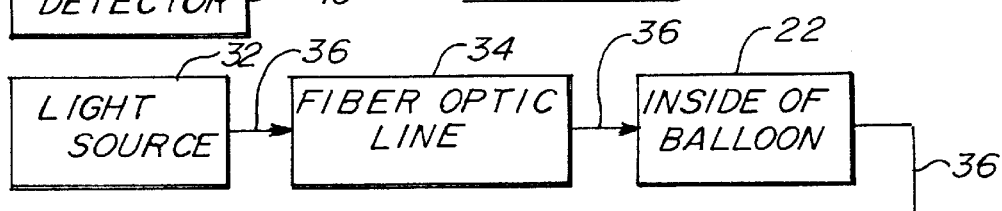
Figure 5:
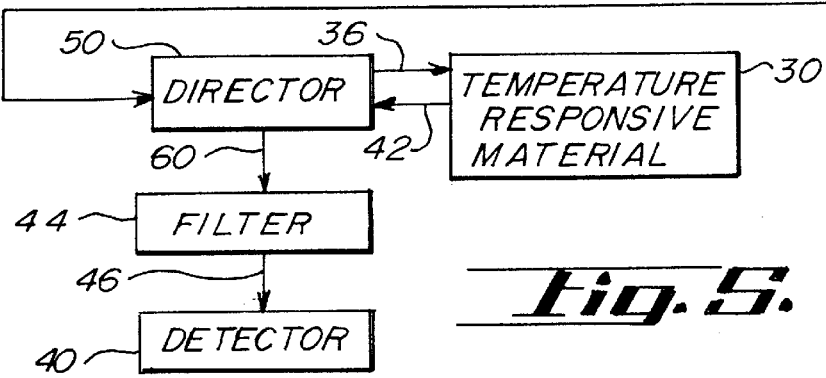

In the embodiment shown the light director 50 may also include filter 44. The filter 44 may be positioned adjacent to the director 50. Where the director 50 is a reflector or mirror, the filter may be positioned beneath the reflective surface 58 of the director 50. The reflective surface 58 may be designed to pass a predetermined wavelength or wavelengths 60 of reflected light 42 therethrough. The predetermined wavelength or wavelengths 60 may then be passed into filter 44 which differentially filters and transmits the received wavelengths to the detector 40 in the manner described above. The pathway of light described in relation to FIG. 2 may be seen in the block diagram shown in FIG. 5 as well.

As previously indicated the detector 40 may be constructed to detect not only specific wavelengths of light received from light reflected off of the material 30, but alternatively or in addition, the detector 40 may detect changes in other properties of the reflected light 42 such as a given wavelength amplitude, frequency, reflectivity, polarization, etc., which may be indicative of a change in the physical property of the material 30, which in turn may indicate the presence of a legion 28.

In should also be noted that the invention may also be directed to the use of alternative spectra of electromagnetic radiation in addition to or as alternatives to the visible light spectrum. Light source 32 may emit any form of radiation as may be appropriate and desired. The various physical changes in the reflected radiation which may be detected by the detector may likewise vary in the manner described.

As may be seen in FIGS. 1 and 2, the light 36 may be transmitted into the balloon 14 via fiber optic line 34. In the embodiment shown in FIG. 3, the light source 32 is a light emitting diode (LED) positioned directly in the inside 22 of the balloon 14. Due to advances in LED technology it is possible to provide a light source 32 which has a significantly reduced size so as to not substantially increase the profile of the catheter 10 if at all. Additionally, an LED may be provided which has minimal heat out put so as to not interfere with the performance of the temperature responsive material 30.

Figure 3:
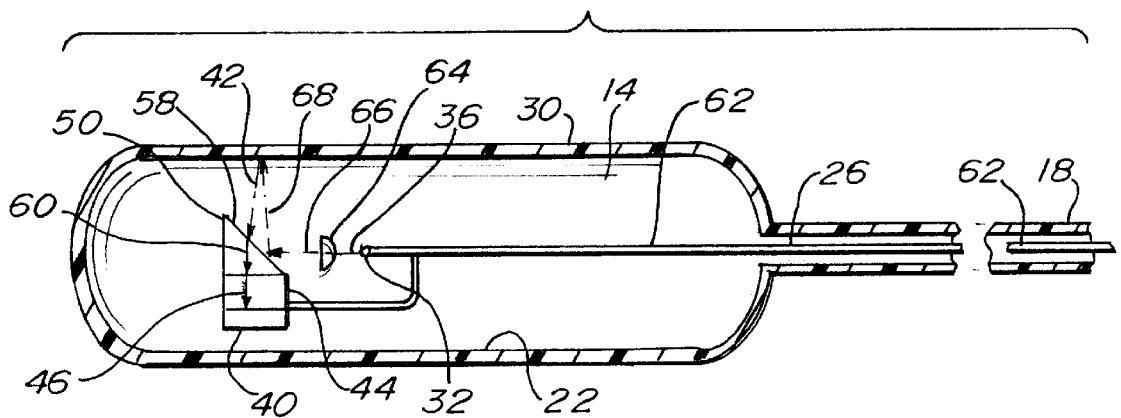
FIG. 3 is a side view of an embodiment of the invention.

In the embodiment shown in FIG. 3 the LED light source 32 obviates the need for the fiber optic line 34 and/or fiber 38, such as may be seen in FIGS. 1 and 2. However, despite the extremely low power consumption of an LED, the light source 32 requires a means of acquiring electrical power. As a result within lumen 26, or through an additional lumen, a conductive member or wire 62 extends from the light source 32 to the proximal end 18 where it is in communication with a power source (not shown).

Figure 6:
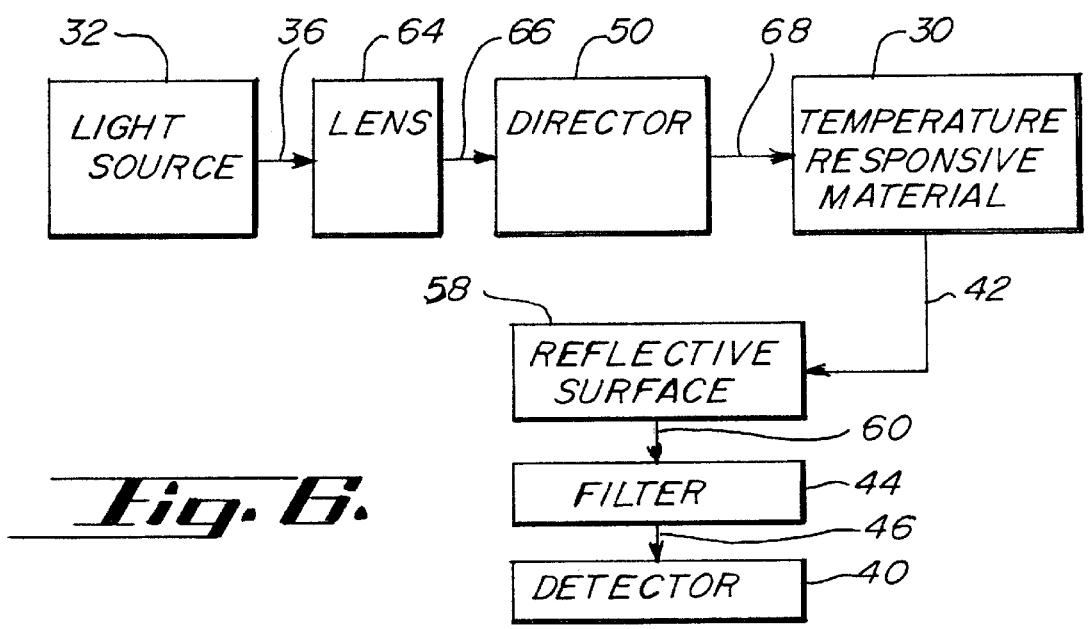
FIG. 6 is a diagrammatic view of the light pathway of the embodiment of the invention shown in FIG. 3.

In the embodiment shown in FIGS. 3 and 6, at least one predetermined wavelength of light 36 is transmitted by the LED light source 32. The light 36 is collimated by a lens 64. The lens 64 may be designed to focus, disperse, filter or otherwise modify the light emitted from the LED 32 as may be desired. The collimated light 66 is then directed to the director 50 where it is at least partially reflected off of the reflective surface 58 of the director 50. The light, now referred to as directed light 68, is then directed to the material 30. At least a portion of the directed light 68 is reflected off of the material 30 and is thereupon referred to as reflected light 42 which is reflected back to the reflective surface 58 of the director 50. A predetermined wavelength or wavelengths 60 of the reflected light 42 is passed through the reflective surface 58 and differentially transmitted through filter 44 to produce at least one predetermined wavelength, or other characteristic as previously discussed, of light 46 which is indicative of the increased temperature of the balloon material 30 associated with the presence of lesion 28. The predetermined characteristic 46 is then detected by detector 40.

Upon detecting the requisite predetermined characteristic 46 of the reflected light 42 which is suggestive of the presence of a lesion 28, the detector may be constructed to transmit a detector signal which notifies a practitioner of the lesion presence. The practitioner may then note the location of the lesion 28 and take further action.

It should be noted that in any of the embodiments described above and shown in FIGS. 1–6 may be combined in whole or in part as desired.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A balloon catheter comprising:
    a catheter, the catheter having a catheter shaft, the catheter shaft having a balloon mounted thereto;
    the balloon at least partially constructed from at least one temperature responsive material which exhibits a predetermined detectable change when the material is in contact with an object having a predetermined temperature, the balloon having an inside and outside;
    at least one lumen extending from the inside of the balloon through the catheter shaft to a proximal end of the catheter shaft, the inside of the balloon in fluid communication with the at least one lumen;
    a light source, the light source constructed and arranged to transmit to the inside of the balloon at least one predetermined wavelength of light, the at least one predetermined wavelength of light being reflected by the at least one temperature responsive material; and
    a detector, the detector constructed and arranged to detect a predetermined reflected light of the at least one predetermined wavelength of light and produce a detector signal.

2. The balloon catheter of claim 1 wherein the light source is positioned in the inside of the balloon.

3. The balloon catheter of claim 2 wherein the light source is a light emitting diode (LED).

4. The balloon catheter of claim 1 wherein the detector is positioned in the inside of the balloon.

5. The balloon catheter of claim 1 wherein the light source comprises at least one optical fiber, the at least one optical fiber further positioned within the at least one lumen and extending from the inside of the balloon to the proximal end of the catheter shaft, the optical fiber constructed and arranged to transmit the at least one predetermined wavelength of light from the proximal end of the catheter shaft to the inside of the balloon.

6. The balloon catheter of claim 1 further comprising a light directing device, the light directing device constructed and arranged to direct the at least one predetermined wavelength of light onto the at least one temperature responsive material in the inside of the balloon.

7. The balloon catheter of claim 6 wherein the light directing device is positioned within the inside of the balloon.

8. The balloon catheter of claim 7 wherein the light directing device is constructed and arranged to move along a longitudinal axis of the inside of the balloon.

9. The balloon catheter of claim 8 wherein the light directing device being further constructed and arranged to rotate about the longitudinal axis of the inside of the balloon.

10. The balloon catheter of claim 9 wherein the light directing device comprising a reflector, the reflector being positioned relative to the light source so as to direct the at least on predetermined wavelength of light to a predetermined location on the inside of the balloon.

11. The balloon catheter of claim 6 further comprising a filter, the filter constructed and arranged to filter at least a portion of the at least one predetermined wavelength of light reflected from the at least one temperature responsive material, and transmit the at least one predetermined color of light to the detector.

12. The balloon catheter of claim 11 wherein the filter is positioned outside of the balloon.

13. The balloon catheter of claim 11 wherein the filter is positioned in the inside of the balloon.

14. The balloon catheter of claim 13 wherein the filter is further positioned adjacent to the light directing device, the light directing device further constructed and arranged to transmit the least a portion of the at least one predetermined wavelength of light reflected from the at least one temperature responsive material to the filter.

15. The balloon catheter of claim 1 wherein the at least one temperature responsive material is a chromatically responsive cholesteric liquid crystal.

16. The balloon catheter of claim 15 wherein the inside of the balloon is transparent to the at least one predetermined wavelength of light, the chromatically responsive cholesteric liquid crystal being positioned between the inside and the outside of the balloon.

17. The balloon catheter of claim 15 wherein the chromatically responsive cholesteric liquid crystal is a coating on the inside of the balloon.

18. The balloon catheter of claim 15 wherein the chromatically responsive cholesteric liquid crystal is selected from the group consisting of: cholesteryl halides; mixed esters of cholesterol and inorganic acids; cholesteryl esters of saturated and unsaturated, substituted and unsubstituted organic acids; cholesteryl ethers and any combinations thereof.

19. The balloon catheter of claim 18 wherein the chromatically responsive cholesteric liquid crystal material is selected from at least one member of the group consisting of: cholesteryl chloride; combinations of cholesteryl bromide and cholesteryl iodide; cholesteryl nitrate; cholesteryl nonanoate; cholesteryl crotonate; cholesteryl chloroformate; cholesteryl chlorodecanoate; cholesteryl chloroeicosanoate; cholesteryl butyrate; cholesteryl caprate; cholesteryl oleate; cholesteryl linolate; cholesteryl linolenate; cholesteryl laurate; cholesteryl erucate; cholesteryl myristate; cholesteryl clupanodonate; oleyl cholesteryl carbonate; cholesteryl heptyl carbamate, decyl cholesteryl carbonate; cholesteryl p-chlorobenzoate; cholesteryl cinnamate; cholesteryl ethers; cholesteryl decyl ether; cholesteryl lauryl ether; cholesteryl oleyl ether; and any combinations thereof.

20. The balloon catheter of claim 6 further comprising at least one lens, the at least one lens positioned in the inside of the balloon, the at least one lens constructed and arranged to collimate the at least one predetermined wavelength of light prior to the light being directed to the at least a portion of the at least one temperature responsive material.

21. The balloon catheter of claim 11 wherein the at least a portion of the at least one temperature responsive material exhibits the predetermined material color, the predetermined material color of the at least one temperature responsive material reflecting the light of the predetermined wavelength, the light of the predetermined wavelength being transmitted by the filter.

22. The balloon catheter of claim 21 wherein the predetermined material color corresponds to the predetermined temperature.

23. The balloon catheter of claim 1 wherein the detector signal is an optically detectable signal.

24. The balloon catheter of claim 1 wherein the detector signal is an electrical signal.

25. The balloon catheter of claim 1 wherein the detector signal is an infrared signal.

26. The balloon catheter of claim 5 wherein the at least one optical fiber is constructed and arranged to transmit the detector signal from the detector to the proximal end of the catheter shaft.

27. A balloon catheter comprising:
a catheter shaft, the catheter shaft having a proximal end, a distal end, and a predetermined length;
a balloon, the balloon mounted to a portion of the distal end of the catheter shaft, the balloon having an uninflated state and being expandable to an inflated state, the balloon further having an inside and an outside, the balloon being made at least partially of at least one temperature responsive material, the at least one temperature responsive material constructed and arranged to exhibit at least one predetermined color when the material is in contact with an object having at least one predetermined temperature;
at least one lumen, the at least one lumen being defined by the catheter shaft and extending from the inside of the balloon to the proximal end of the catheter shaft, the first lumen being in fluid communication with the inside of the balloon;
at least one optical fiber, the at least one optical fiber extending from the proximal end of the catheter shaft to the inside of the balloon, the at least one optical fiber having a first end positioned at the proximal end of the catheter shaft and a second end positioned in the inside of the balloon;
a light source the light source constructed and arranged to transmit light;
a light director, the light director constructed and arranged to direct the light received from the light source transmitted from the proximal light source through the at least one optical fiber onto a portion of the at least one temperature responsive material of the balloon; and
a light detector, the light detector constructed and arranged to detect at least one predetermined color of light and thereupon transmit a detector signal.

28. The balloon catheter of claim 27 wherein the light director comprises a reflector, the reflector having at least one reflecting surface, the reflector constructed and arranged to reflect at least a portion of the light transmitted by the light source onto at least a portion of the at least one temperature responsive material, the at least a portion of the light characterized as directed light.

29. The balloon catheter of claim 28 further comprising a filter, the at least a portion of the at least one temperature responsive material further constructed and arranged to reflect at least a portion of the directed light onto the filter, the at least a portion of the directed light comprising the reflected light, the filter constructed and arranged to filter at least a portion of the reflected light and transmit the at least one predetermined color of light to the detector.

30. The balloon catheter of claim 29 wherein the filter is positioned below the at least one reflective surface of the reflector.

31. The balloon catheter of claim 30 wherein the reflector surface is constructed and arranged to permit passage of the at least a portion of the reflected light therethrough.

32. A method of detecting a lesion in a body lumen comprising the steps of:
inserting the balloon catheter of claim 11 into a body lumen;
advancing the distal end of the catheter shaft to a portion of the body lumen;
expanding the balloon so that the balloon contacts the portion of the body lumen;
emitting a light from the light source;
directing the light onto the at least a portion of at least one temperature responsive material;
reflecting the light from the at least a portion of at least one temperature responsive material to a filter;
filtering the light received by the filter to at least one predetermined color of light, the at least one predetermined color of light corresponding to at least one predetermined temperature of the at least a portion of at least one temperature responsive material; and
detecting the at least one predetermined color of light with the detector.

33. The method of claim 32 wherein a vulnerable plaque lesion is indicated by the at least a portion of at least one temperature responsive material exhibiting the predetermined material color.

34. The method of claim 33 further including the step of mapping the vulnerable plaque lesion by observing the predetermined material color.

35. The method of claim 34 further including the step of classifying a lesion based on the at least one predetermined color of light detected by the detector.

\* \* \* \* \*